United States Patent
Mudduluru et al.

(10) Patent No.: US 9,567,292 B2
(45) Date of Patent: Feb. 14, 2017

(54) PROCESS FOR PREPARATION OF 2,3-DIHYDROXY BENZONITRILE

(71) Applicant: Laurus Labs Private Limited, Hyderabad (IN)

(72) Inventors: Hari Krishna Mudduluru, Hyderabad (IN); Shankar Madhavaram, Hyderabad (IN)

(73) Assignee: Laurus Labs Private Limited, Hyderabad (IN)

( * ) Notice: Subject to any disclaimer, the term of this patent is extended or adjusted under 35 U.S.C. 154(b) by 177 days.

(21) Appl. No.: 14/415,527

(22) PCT Filed: Jul. 18, 2013

(86) PCT No.: PCT/IN2013/000447
§ 371 (c)(1),
(2) Date: Jan. 16, 2015

(87) PCT Pub. No.: WO2014/013512
PCT Pub. Date: Jan. 23, 2014

(65) Prior Publication Data
US 2015/0175532 A1    Jun. 25, 2015

(30) Foreign Application Priority Data
Jul. 19, 2012 (IN) .......................... 2926/CHE/2012

(51) Int. Cl.
*C07C 253/30*     (2006.01)
*C07C 231/02*     (2006.01)
*C07C 253/20*     (2006.01)

(52) U.S. Cl.
CPC .......... *C07C 253/30* (2013.01); *C07C 231/02* (2013.01); *C07C 253/20* (2013.01)

(58) Field of Classification Search
CPC .................................................. C07C 253/30
See application file for complete search history.

(56) References Cited

FOREIGN PATENT DOCUMENTS

GB        967605 A     8/1964
JP      S54128542 A    10/1979

OTHER PUBLICATIONS

Raymond J. Bergeron, et al., "Partition-Variant Desferrithiocin Analogues: Organ Targeting and Increased Iron Clearance", Journal of Medicinal Chemistry, 2005, vol. 48, No. 3, pp. 821-831.

*Primary Examiner* — Shawquia Jackson
(74) *Attorney, Agent, or Firm* — Blank Rome LLP; Brian W. Higgins

(57) ABSTRACT

The present invention relates to one pot process for the preparation of 2,3-dihydroxy benzonitrile from 2,3-dialkoxy benzoic acid without prior isolation of the intermediates. Further the invention relates to the preparation of 2,3-dihydroxy benzonitrile by dealkylation of 2,3-dialkoxy benzonitrile using suitable aluminum salt-amine complex.

20 Claims, No Drawings

PROCESS FOR PREPARATION OF 2,3-DIHYDROXY BENZONITRILE

PRIORITY

This application claims the benefit under Indian Provisional Application No. 2926/CHE/2012 filed 19 Jul. 2012 and entitled "AN IMPROVED PROCESS FOR THE PREPARATION OF 2,3-DIHYDROXY BENZONITRILE", the content of which is incorporated by reference herein.

FIELD OF THE INVENTION

The present invention relates to one pot synthesis of 2,3-dihydroxy benzonitrile from 2,3-dialkoxy benzoic acid without isolating any intermediates.

BACKGROUND OF THE INVENTION

The substituted catechol compounds have a great commercial importance in the synthesis of pharmaceutical compounds. 2,3-dihydroxy benzonitrile of Formula I, a substituted catechol compound is an important starting material for the preparation of a number of valuable heterocyclic compounds which are medicinally important. 2,3-dihydroxy benzonitrile is the key starting material for Desferrithiocin and its analogues. Desferrithiocin (DFT) is an orally effective iron chelator, with a similar high affinity and selectivity for iron to desferrioxamine (DFO), which has been shown clinically to possess antineoplastic activity. Therefore the commercial production for 2,3-dihydroxy benzonitrile is utmost important.

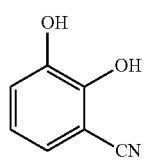

Formula I

Several conventional processes for the preparation of 2,3-dihydroxy benzonitrile are available in the literature. Various other procedures in the literature cites the preparation of 2,3-dihydroxy benzonitrile from different starting materials (substituted catechol compounds). A practically more suitable process for the preparation of 2,3-dihydroxy benzonitrile is from the corresponding precursor 2,3-dialkoxy benzoic acid. A person skilled in the art expects the process to proceed from acid halide, amide, nitrile and dealkylation, wherein the dealkylation step is mandatory to obtain the title compound, *Chemical and Pharmaceutical bulletin* vol. 58, 11, 2010, 1552-1553 discloses the process for preparation of 2,3-dihydroxy benzonitrile from 2,3-dihydroxy benzaldehyde in the presence of formic acid, hydroxylamine hydrochloride and sodium formate.

*European Journal of Organic Chemistry* 11, 2006, 2513-2516 discloses the process for preparation of 2,3-dihydroxy benzonitrile from 1,3-benzodioxole-4-carbaldehyde. Oxidative conversion of aldehydes to nitriles and deprotection of hydroxy groups done in the presence of 2.2 eq of sodium hexamethyldisilazane in tetrahydrofuran and in highly polar solvent 1,3-Dimethyl-2-imidazolidinone at 185° C. in a sealed tube.

Several reviews have been described for deprotection of phenolic ethers. For example, phenolic methyl ethers have deprotected to remove the methyl moiety using hydrogen halide such as hydrogen chloride or hydrogen bromide under highly acidic conditions; highly dark colored products formed in these reactions. In addition the phenolic compounds react further with the halogen compounds used thus setting a major drawback on this route.

Use of Lewis acids such as aluminum chloride or aluminum bromide in dealkylation is well known in the art. U.S. Pat. No. 7,253,324 discloses a process of poly O-dealkylation of alkoxy aromatic compounds using a aluminum chloride-N,N-dimethylaniline complex. However the patent restricts towards manufacture of polyphenols such as Resveratrol, Oxyresveratrol and Gnetol.

A conventional process for producing 2,3-dihydroxy benzonitrile from 2,3-dimethoxy benzonitrile is disclosed in *Journal of Medicinal Chemistry,* 2005, Vol. 48, No. 3, 821-831. The disclosed process appears to be the closest prior art involving demethylation in the presence of boron tribromide in dichloromethane.

Boron tribromide is highly moisture sensitive, colorless fuming liquid and decomposes in air with evolution of HBr. It is stored under a dry inert atmosphere and transferred by syringe or through a Teflon tube for the reactions. It reacts violently with protic solvents such as water and alcohols. However the aforementioned process for preparing 2,3-dihydroxy benzonitrile are less than fully satisfactory in view of hazardous reagents, difficult to handle, expensive, lower temperatures, long reaction times, tedious work up procedures, not liable for scale up process and low reaction yields, thereby limiting their use in commercial scale production.

Despite all prior advances, available methods for synthesizing 2,3-dihydroxy benzonitrile from 2,3-dialkoxy benzoic acid which proceed through known intermediates such as the corresponding acid 2,3-dialkoxy benzoyl chloride, 2,3-dialkoxy benzamide, 2,3-dialkoxy benzonitrile remain labor intensive, time consuming and environmentally unfavorable. The isolated intermediates are however available in the literature, wherein the isolation of the intermediated are time consuming and practically not suitable for manufacturing scales. Thus, there remains a need for a simple, cost effective, industrially feasible and scalable process for the synthesis of 2,3-dihydroxy benzonitrile that would avoid the aforementioned difficulties.

The present inventors thus found an alternate approach for preparing 2,3-dihydroxy benzonitrile involving a one-pot synthesis from 2,3-dialkoxy benzoic acid without isolating any intermediates and also involving the use of aluminum salt-amine complex for the dealkylation process.

SUMMARY OF THE INVENTION

The present invention encompasses a one pot process for preparing 2,3-dihydroxy benzonitrile with high product yield and quality.

In according with one embodiment, the present invention provides a one-pot process for the preparation of 2,3-dihydroxy benzonitrile of Formula I,

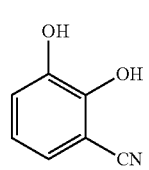

Formula I comprising the steps of:
   a) reacting an acid compound of Formula (II)

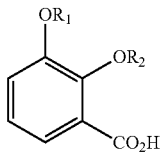

Formula II wherein $R_1$ and $R_2$ are independently represents H or $C_{1-4}$ alkyl group with a suitable halogenating reagent in presence of a suitable solvent to obtain corresponding benzoic acid halide,
   b) reacting the resulting benzoic acid halide compound with a source of ammonia to obtain corresponding amide of Formula III;

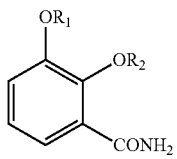

Formula III c) treating the amide compound with a suitable dehydrating reagent to obtain dialkoxy benzonitrile compound of Formula IV, and

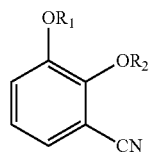

Formula IV d) dealkylating the resulting dialkoxy benzonitrile compound with a suitable dealkylating agent;
   wherein the steps a) to d) are carried out in a single step without isolating any intermediates.

In according with a second embodiment, the present invention provides a one-pot process for the preparation of 2,3-dihydroxy benzonitrile, comprising the steps of:
   a) reacting an acid compound of Formula II, wherein $R_1$ and $R_2$ are independently represents H or $C_1$ alkyl group with a suitable halogenating reagent in presence of a suitable solvent to obtain corresponding benzoic acid halide,
   b) quenching the resulting benzoic acid halide compound in to a solution of aqueous ammonia to obtain corresponding amide of Formula III,
   c) treating the resulting solution of amide compound with a suitable dehydrating reagent to obtain dialkoxy benzonitrile compound of Formula IV, and
   d) dealkylating the resulting solution of dialkoxy benzonitrile compound with aluminum salt-amine complex to obtain 2,3-dihydroxy benzonitrile of Formula I.

In according with a third embodiment, the present invention provides a process for preparation of 2,3-dihydroxy benzonitrile of Formula I, comprising: deprotecting dialkoxy benzonitrile compound of Formula IV; wherein $R_1$ and $R_2$ are independently represents H or $C_{1-4}$ alkyl group, with a suitable dealkylating agent in a suitable organic solvent, wherein the dealkylating agent is aluminum salt-amine complex.

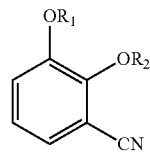

Formula IV

In according with a fourth embodiment, the present invention provides a process for preparation of 2,3-dihydroxy benzonitrile of Formula I, comprising: deprotecting dialkoxy benzonitrile compound of Formula IV, wherein $R_1$ and $R_2$ are independently represents H or $C_{1-4}$ alkyl group, with aluminum salt-amine complex in a suitable organic solvent; wherein the aluminium salt is selected from the group comprising aluminium chloride, aluminium bromide, aluminium iodide and the like and mixtures thereof; and amine is a compound of formula NRaRbRc;
in which:
Ra, Rb and Rc independently represents a hydrogen, a linear or branched alkyl group, a linear or branched $C_2$-$C_6$ alkenyl group, a $C_1$-$C_6$ alkanol, a $C_3$-$C_{10}$ cycloalkyl group, a cycloalkylalkyl group, an aryl group, an aralkyl group or Ra, Rb or Rc may form a cyclic ring with nitrogen.

DETAILED DESCRIPTION OF THE INVENTION

The present invention provides one pot process for the preparation of 2,3-dihydroxy benzonitrile from 2,3-dialkoxy benzoic acid suitable for the large scale preparation.

In according with one embodiment, the present invention provides a one-pot process of 2,3-dihydroxy benzonitrile of Formula I,

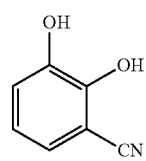

Formula I comprising the steps of:
   a) reacting an acid compound of Formula (II)

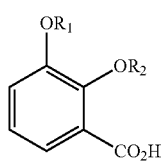

Formula II wherein $R_1$ and $R_2$ are independently represents H or $C_{1-4}$ alkyl group with a suitable halogenating reagent in presence of a suitable solvent to obtain corresponding benzoic acid halide, b) reacting the resulting benzoic acid halide compound with a source of ammonia to obtain corresponding amide of Formula III;

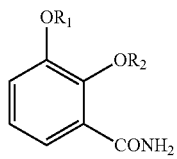

Formula III c) treating the amide compound with a suitable dehydrating reagent to obtain dialkoxy benzonitrile compound of Formula IV, and

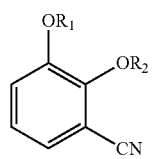

Formula IV d) dealkylating the resulting dialkoxy benzonitrile compound with a suitable dealkylating agent.

In another embodiment, the present invention provides a one-pot process of 2,3-dihydroxy benzonitrile of Formula I, wherein the entire process is carried out in a single step without isolating any process intermediates.

In a preferred embodiment, the starting compound of Formula II is

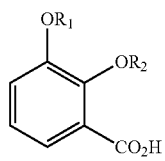

Formula II in which $R_1$ and $R_2$ are independently, represents H or $C_{1-4}$ alkyl group; preferably methyl, ethyl, propyl, isopropyl, ter-butyl; more preferably $R_1$ and $R_2$ are methyl.

The starting material, a compound of Formula II is known in the art and can be prepared by any known method, for example starting compound of Formula II can be synthesized as disclosed in *Journal of the American Chemical Society* vol. 62; (1940), 1963-1965 or *Synthetic Communications*; vol. 25, nb. 14, (1995), 2121-2134, which are included by reference herein in its entirety.

In an embodiment of the present invention, the halogenation of 2,3-dialkoxy benzoic acid, preferably 2,3-dimethoxy benzoic acid of aforementioned step a can be carried out by using a suitable halogenating agent. The halogenating agent is preferably selected from the group consisting of phosphorous trichloride, phosphorus penta chloride, phosphorus oxychloride, thionyl chloride and sulfuryl chloride. More preferably the halogenating agent may be either thionyl chloride or phosphorus oxychloride.

The halogenation of 2,3-dimethoxy benzoic acid of step a can be carried out in a suitable solvent. The suitable solvent for halogenation is selected from the group consisting of chloroform, dichloromethane, toluene, tetrahydrofuran and dioxane, and preferably dichloromethane.

The halogenation of 2,3-dimethoxy benzoic acid can be carried out at a temperature of about 20° C. to about 50° C.; more preferably about 20° C. to about 35° C.

Optionally catalytic amount of an amide reagent may be added to the halogenation reaction. The suitable amide reagent is dimethyl formamide.

After completion of the reaction, the reaction mass obtained in step (a) as such may be treated with a source of ammonia to obtain 2,3-dimethoxy benzamide of Formula III.

The source of ammonia in step (b) is selected from the group comprising ammonia gas, ammonium chloride or aqueous ammonia; preferably aqueous ammonia.

In a preferred embodiment, the step a) reaction solution may be quenched into a solution of pre-prepared aqueous ammonia solution at a temperature of about 0° C. to about 30° C.; more preferably about 10° C. to about 15° C. to obtain 2,3-dimethoxy benzamide of Formula III.

After completion of the step b) reaction, the organic and aqueous layers may be separated and the organic layer is concentrated at a temperature of about 45-50° C. to obtain Formula III as oily residue, which on further diluted with a suitable water immiscible organic solvent and co-distilling the solvent at a temperature of about 55-60° C. until the moisture content of the reaction solution reaches to about 0.5% and proceed further to the step c).

The suitable water immiscible organic solvent includes, but is not limited to esters such as methyl acetate, ethyl acetate and the like; aromatic hydrocarbons such as toluene, xylene and the like; ethers such as tetrahydrofuran and the like; and mixtures thereof; preferably toluene.

Step c) of the aforementioned step includes treating the solution of amide compound obtained from step b) with a suitable dehydrating reagent to obtain dimethoxy benzonitrile compound of Formula IV.

The dehydration reagent used is selected from the group consisting of oxyaloyl chloride, oxyaloyl bromide, oxyaloyl iodide, phosphorous trichloride, phosphorous tribromide, phosphorous triiodide, thionyl chloride, thionyl bromide, thionyl iodide, phosphorous pentachloride, phosphorus pentoxide, phosphorous oxy chloride, ethyl dichlorophosphate and the like; preferably thionyl chloride, phosphorus oxychloride; more preferably phosphorus oxychloride.

The dehydration of 2,3-dimethoxy benzamide of step (c) may be carried out at a temperature of about 40° C. to about 90° C.; more preferably about 75° C. to about 85° C.

After completion of the dehydration reaction, the reaction mass obtained in step (c) may be quenched into water and separating the aqueous and organic layers. The resultant organic layer containing product may be subjected to azeotropic distillation at a temperature of about 95-120° C.; preferably at about 105-115° C. to removing the water from the organic layer and the obtained organic layer containing dimethoxy benzonitrile compound of Formula IV can be further processed directly for the step d) of dealkylation reaction.

In another embodiment, the present invention provides a process for the preparation of 2,3-dihydroxy benzonitrile of Formula I, comprising deprotecting dialkoxy benzonitrile of compound of Formula IV; wherein $R_1$ and $R_2$ are independently represents H or $C_{1-4}$ alkyl group, preferably methyl, as obtained by the process described above or may be obtained by any known process, as a starting material or as an intermediate with a suitable dealkylating agent in a suitable organic solvent.

In another embodiment, the present invention provides a process for preparation of 2,3-dihydroxy benzonitrile of Formula I, comprising: deprotecting dialkoxy benzonitrile compound of Formula IV; preferably dimethoxy benzonitrile compound of Formula IV obtained by any known process or obtained by the process as described above with a suitable dealkylating agent in a suitable organic solvent, wherein the dealkylating agent is aluminum salt-amine complex.

The aluminium salt include, but is not limited to aluminium chloride, aluminium bromide, aluminium iodide and the like and mixtures thereof; preferably aluminium chloride.

The amine in the fore going process may be a compound of Formula NRaRbRc;
in which:
Ra, Rb and Rc independently represents a hydrogen, a linear or branched alkyl group, a linear or branched $C_2$-$C_6$ alkenyl group, a $C_1$-$C_6$ alkanol, a $C_3$-$C_{10}$ cycloalkyl group, a cycloalkylalkyl group, an aryl group, an aralkyl group or Ra, Rb or Rc may form a cyclic ring with nitrogen.

The amine may be in the form of its free amine or its acceptable salt form.

The linear or branched alkyl group includes, but is not limited to methyl, ethyl, n-propyl, isopropyl, butyl, isobutyl, sec-butyl, tert-butyl, pentyl, hexyl, heptyl, octyl, ethylhexyl and the like; the linear or branched $C_2$-$C_6$ alkenyl group includes, but is not limited to an ethenyl or vinyl, propenyl or allyl, 1-propenyl, n-butenyl, isobutenyl, 3-methylbut-2-enyl, n-pentenyl or hexenyl group and the like; the $C_1$-$C_6$ alkanol includes, but is not limited to methanol, ethanol, propanol, butanol, and the like; the $C_3$-$C_{10}$ cycloalkyl group includes, but is not limited to cyclopropyl, cyclohexyl and the like; the cycloalkylalkyl group includes, but is not limited to cyclopropylmethyl, cyclobutylmethyl, cyclopentylmethyl, cyclohexylmethyl, cycloheptylmethyl, cyclopropylethyl or cyclohexylethyl group and the like; the aryl group includes, but is not limited to phenyl, naphthyl, indenyl or anthracenyl and the like; and the aralkyl includes, but is not limited to benzyl, 1-phenylethyl, naphthalenylmethyl or 1-naphthalenylethyl and the like.

Preferably, the amine can be selected from the group consisting of diethylamine, diisopropyl amine, di-n-propylamine, diisobutylamine, diallylamine, allylmethyl amine, diphenylamine, dibenzylamine, trimethylamine, triethylamine, tripropylamine, tributylamine, benzylethyl amine, methylbenzyl amine, N,N-dimethylethylamine, N,N-diethylmethylamine, N,N-dimethylbutylamine, dicyclopropylamine, dicyclohexylamine, N-t-butyl cyclohexylamine, N-isobutyl cyclohexylamine, di(2-ethylhexyl)amine, dicyclohexylmethyl amine, N,N-dimethylaniline, N,N-diethylaniline, N-methyl-N-ethyl aniline, N-methyl-N-isopropyl aniline, 1-N,N-dimethylnaphthalene, 2-N,N-dimethyl naphthalene, 2,6-lutidine and the like and mixtures thereof; more preferably the amine is triethyl amine or dimethylaniline.

The suitable organic solvent for the dealkylation includes but is not limited to esters, ketones, amides, nitrites, ethers, halogenated hydrocarbons, aromatic hydrocarbons and mixtures thereof. The esters include, but are not limited to methyl acetate, ethyl acetate, isopropyl acetate and the like; ketones include, but are not limited to acetone, methyl isobutyl ketone, methyl ethyl ketone and the like; amides include, but are not limited to dimethyl formamide, dimethyl acetamide, N-methyl pyrrolidinone and the like; nitriles include, but are not limited to acetonitrile, propionitrile and the like; ethers include, but are not limited to tetrahydrofuran, dimethyl ether, diisopropyl ether, methyl tertiary butyl ether, 1,4-dioxane and the like; halogenated hydrocarbons include, but are not limited to methylene chloride, ethylene chloride, chloroform, carbon tetrachloride and the like; aromatic hydrocarbons include, but are not limited to toluene, xylene and the like. Preferably the solvent is chosen from either chlorinated aliphatic solvents like methylene chloride, ethylene chloride, chloroform, carbon tetrachloride or the aromatic hydrocarbon like toluene, xylenes and the like; preferably the suitable solvent is toluene.

The entire process for the preparation of 2,3-dihydroxy benzonitrile form 2,3-dialkoxy benzoic acid is schematically represented as follows:

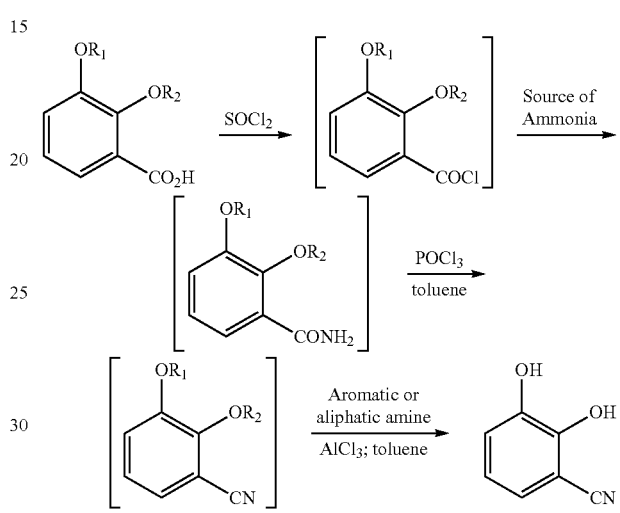

Another aspect of the invention, relates to the formation of mono dealkylated benzonitrile impurities in the specified limitations, thus enhancing the purity and yield of the 2,3-dihydroxy benzonitrile. The mono dealkyated impurities as cited herein are represented as follows:

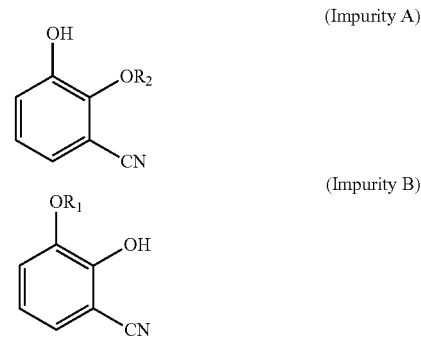

The process of the present invention advantageously provide 2,3-dihydroxy benzonitrile in relatively high purity, i.e., a purity of greater than or equal to about 99% as measure by HPLC, and more preferably greater than or equal to about 99.5%; and substantially free of impurities A and B.

As used herein, the term "substantially free" refers to 2,3-dihydroxy benzonitrile having less than 0.1% by HPLC of impurity A or impurity B; particularly less than 0.05% by HPLC of impurity A or impurity B.

The present invention provides 2,3-dihydroxy benzonitrile, obtained by the above process, as analyzed using high performance liquid chromatography ("HPLC") with the conditions described below:

| | |
|---|---|
| Column | Inertsil ODS 3V (150 × 4.6) mm, 5 µm |
| Column temperature | 30° C. |
| Mobile phase | Mobile Phase-A: 10 mM $KH_2PO_4$ pH adjusted to 3.0 with ortho phosphoric acid Mobile Phase-B: Acetonitrile |
| Diluent | Water:Acetonitrile (1:1) |
| Flow rate | 1.0 ml/min |
| Wavelength | 210 nm |
| Injection Volume | 10 µL |
| Run time | 30 min |

The advantages of the present invention thus encompass:
1. A cost effective process,
2. Time saving process as it doesn't involves any isolation of the intermediates, which would enhance more time consumption during isolations,
3. Industrially feasible for scaleup.
4. Decreased impurity profile.

The process of the present invention optionally comprises, a step of collecting 2,3-dihydroxy benzonitrile form the reaction mixture by at least one procedure selected from precipitation, recrystallisation, or by distillation.

The foregoing process thus mentioned above, to prepare 2,3-dihydroxy benzonitrile is a useful starting material for the preparation of various heterocyclic compounds.

EXAMPLES

The following examples are provided to enable one skilled in art to practice the invention and are merely illustrative of the invention. The examples should not be read as limiting the scope of the invention as defined in the claims.

Example 1

Preparation of 2,3-dihydroxy benzoic acid form 2,3-dimethoxy benzoic acid

To a stirred solution of 2,3-dimethoxy benzoic acid (100 g; 0.549 mol) in dichloromethane (500 mL) and catalytic amount of DMF (~2 mL) at a temperature about 30-35° C., thionyl chloride (130.6 g; 1.102 mol) was added and stirred for a period of two hours. Reaction was monitored by TLC for completion of the starting material (NMT-5%). If reaction not completed added thionyl chloride (9.8 g; 0.823 mol). Upon completion of reaction, the reaction mass was quenched in to the −5° C. chilled aqueous ammonia (580 mL) solution at a temperature below 15° C. under stirring. The reaction mass was stirred at temperature 30-35° C. over a period of 30 min. The separated organic fraction was concentrated under atmospheric distillation at below 50° C., charged toluene (100 ml) and co-distilled until the reaction mass moisture content become less than 0.5%. The obtained benzamide compound was dissolved in toluene (500 mL) at temperature about 30-35° C. To the reaction mass was added $POCl_3$ (126.3 g; 0.824 mol). The temperature of the reaction mass was raised to 80-85° C. and maintained over a period of 1-2 hours for the completion of the reaction (Progress of the reaction was monitored by HPLC until the benzamide NMT 1.0%). If the reaction was not completed, added second lot of $POCl_3$ (10.1 g; 0.06 mol) at 30-35° C. The reaction mass was cooled to a temperature about 30-35° C. upon completion of the reaction. The reaction mixture was added to cold water (1000 mL) at 0-5° C. The organic fraction was separated and washed with 8% sodium bicarbonate solution. The organic fraction was separated and azeotropic distilled at 110-115° C. (until moisture content NMT 0.2%), after reaching moisture content to normal limit cooled the reaction mass temperature to 40° C. and distilled reaction mass volume becomes ~3 volumes under vacuum at a temperature 40-50° C. After distillation cooled the reaction mass temperature to 30-35° C. In another RB flask charged toluene (160 ml), triethyl amine (199.7 g; 1.977 mol) at 30-35° C. and stirred for 10 min. charged aluminum chloride (52.7 g×5; 1.977 mol) in five lots with the gap of 10 min between each lot addition (addition of aluminum chloride may raise the temperature to 45-50° C.). The reaction mass temperature was raised to about 70-75° C. and added above reaction mass (methoxy compound) for 30 min. maintained the reaction mass at 70-75° C. for 8 hr. Progress of the reaction was monitored by HPLC (until the 2,3-dimethoxybenzonitrile content 0.25% and 3-methoxy-2-hydroxybenzonitrile content 0.2%). If reaction was not completed added second lot of triethyl amine (27.7 g; 0.27 mol) and aluminum chloride (36.6 g; 0.27 mol). Upon completion of the reaction, the reaction mixture was cooled to 30-35° C. and quenched with chilled aqueous HCl (prepared by addition of water (500 ml) and Conc. HCl (500 ml)) at 15° C. Stirred reaction mass at 25-30° C. for about 30 min, filtered the obtained solids and separated aqueous and organic layers. Charged MIBK (320 ml) to the solids and charged above aqueous layer, filtered through celite and separated aqueous and organic layers. To the aqueous layer given MIBK (320+160 ml) extractions. To the combined organic layer given 20% sodium chloride solution washing, organic layer was azeotropic distilled at 110° C. to remove the water (moisture content NMT 0.2%). Cooled the reaction mass temperature to 30° C. and filtered through 0.45 micron/1 micron filter. To the filtrate charged 1% EDTA (400 ml), stirred for 30 min and filtered through 10 micron cloth. The organic fraction was separated and distilled off to obtain the residue. The residue was treated with dichloromethane (400 ml) and the solid obtained was filtered and dried under vacuum over 6 hr at 60-65° C. to obtain the title compound 2,3-dihydroxy benzonitrile. (56 g, yield 75.4%)
Purity by HPLC 99.81%;
Impurity A: 0.05%
Impurity B: 0.07%

Example 2

Preparation of 2,3-dihydroxy benzoic acid form 2,3-dimethoxy benzoic acid

To a stirred solution of 2,3-dimethoxy benzoic acid (250 g; 1.372 mol) in dichloromethane (1250 mL) and catalytic amount of DMF (~5 mL) at a temperature about 25-30° C., thionyl chloride (326.5 g; 2.745 mol) was added and stirred for a period of two hours. Upon completion of reaction, the reaction mass was added to the super cooled aqueous ammonia (1450 mL) solution at a temperature about 0-5° C. under stirring. The reaction mass was stirred at temperature 0-5° C. over a period of 60 min. The separated organic fraction was concentrated under atmospheric distillation at below 50° C., followed by azeotropic distillation with addition of toluene (250 mL) to the concentrate. The obtained benzamide compound was dissolved in toluene (1250 mL) at temperature about 25-30° C. To the benzamide compound in toluene as above, POCl$_3$ (340.2 g; 2.3 mol) was added. The temperature of the reaction mass was raised to 75-80° C. and maintained over a period of 1-2 hours for the completion of the reaction. The reaction mass was cooled to a temperature about 25-30° C. upon completion of the reaction. The reaction mixture was added to cold water (2500 mL) at 0-5° C. The organic fraction was separated and washed with sodium bicarbonate solution. The organic fraction was separated and distilled under vacuum at a temperature 40-50° C. The benzonitrile compound was dissolved in toluene (475 mL) at room temperature added to a solution of toluene (675 mL) containing dimethyl aniline (498.36 g; 4.11 mol), anhydrous aluminum chloride (549.02 g; 4.11 mol). The reaction mass was raised to a temperature about 110-120° C. and maintained over completion about 1-2 hours. Upon completion of the reaction, the reaction mixture was quenched with aqueous HCl at a temperature below 20° C. (preferred 0-5° C.). To the quenched reaction mass MIBK was added and stirred. The organic fraction was separated and treated with water; brine solution individually. The organic fraction was separated and distilled off to obtain the residue. The residue was treated with dichloromethane and the solid obtained was filtered and dried under vacuum over 6 hr period at 55-60° C. to obtain the title compound 2,3-dihydroxy benzonitrile. (127 g, over all yield ~70%)

Purity by HPLC 99.68%;
Impurity A: 0.07%
Impurity B: 0.10%

While the invention has been described with reference to above detailed description and the preferred examples, it is not intended to be limited thereto. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the specification appended hereto.

We claim:

1. A one-pot process for the preparation of 2,3-dihydroxy benzonitrile of Formula I,

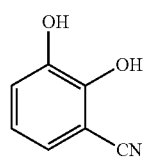

Formula I comprising the steps of:
a) reacting an acid compound of Formula II

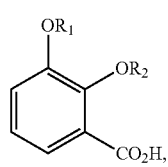

Formula II wherein R$_1$ and R$_2$ are each independently H or C$_{1-4}$ alkyl group, with a halogenating reagent in presence of a solvent to obtain a corresponding benzoic acid halide;
b) reacting the benzoic acid halide with a source of ammonia to obtain a corresponding amide of Formula III

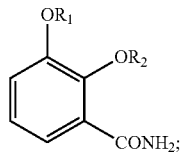

Formula III c) treating the amide compound with a dehydrating reagent to obtain the compound of Formula IV

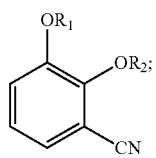

Formula IV and
d) dealkylating the compound of Formula IV with a dealkylating agent in an organic solvent;
wherein the steps a) to d) are carried out in a single step without isolating any intermediates.

2. The process of claim 1, wherein the C$_{1-4}$ alkyl is selected from the group consisting of methyl, ethyl, propyl, isopropyl, and ter-butyl.

3. The process of claim 1, wherein the halogenating reagent is selected from the group consisting of phosphorous trichloride, phosphorus penta chloride, phosphorus oxychloride, thionyl chloride and sulfuryl chloride.

4. The process of claim 1, wherein the solvent for step a) is selected from the group consisting of chloroform, dichloromethane, toluene, tetrahydrofuran and 1,4-dioxane.

5. The process of claim 1, wherein the step a) is carried out at a temperature of about 20° C. to about 50° C.

6. The process of claim 1, wherein the source of ammonia is ammonia gas, ammonium chloride or aqueous ammonia.

7. The process of claim 1, wherein the step b) is carried out by quenching the step a) reaction mass into the source of ammonia at a temperature of about 0° C. to about 30° C.

8. The process of claim 1, wherein the dehydrating reagent is selected from the group consisting of oxyaloyl chloride, oxyaloyl bromide, oxyaloyl iodide, phosphorous trichloride, phosphorous tribromide, phosphorous triiodide, thionyl chloride, thionyl bromide, thionyl iodide, phosphorous pentachloride, phosphorus pentoxide, phosphorous oxy chloride and ethyl dichlorophosphate.

9. The process of claim 1, wherein step c) is carried out at temperature of about 40° C. to about 90° C.

10. The process of claim 1, wherein the dealkylating agent is an aluminium salt-amine complex.

11. The process of claim 10, wherein the aluminium salt is selected from the group consisting of aluminium chloride, aluminium bromide and aluminium iodide.

12. The process of claim 10, wherein the amine is selected from a compound of formula NRaRbRc;

Wherein Ra, Rb and Rc independently represents a hydrogen, a linear or branched alkyl group, a linear or branched $C_2$-$C_6$ alkenyl group, a $C_1$-$C_6$ alkanol, a $C_3$-$C_{10}$ cycloalkyl group, a cycloalkylalkyl group, an aryl group, an aralkyl group.

13. The process of claim 12, wherein the amine is selected from the group consisting of diethylamine, diisopropyl amine, di-n-propylamine, diisobutylamine, diallylamine, allylmethyl amine, diphenylamine, dibenzylamine, trimethylamine, triethylamine, tripropylamine, tributylamine, benzylethyl amine, methylbenzyl amine, N,N-dimethylethylamine, N,N-diethylmethylamine, N,N-dimethylbutylamine, dicyclopropylamine, dicyclohexylamine, N-t-butyl cyclohexylamine, N-isobutyl cyclohexylamine, di(2-ethylhexyl) amine, dicyclohexylmethyl amine, N,N-dimethylaniline, N,N-diethylaniline, N-methyl-N-ethyl aniline, N-methyl-N-isopropyl aniline, 1-N,N-dimethylnaphthalene, 2-N,N-dimethyl naphthalene and 2,6-lutidine.

14. The process of claim 10, wherein the aluminium salt-amine complex is aluminium chloride-N,N-dimethylaniline complex or aluminium chloride-triethylamine complex.

15. A process for preparation of 2,3-dihydroxy benzonitrile of Formula I,

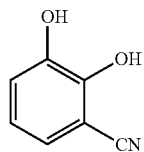

Formula I comprising the step of deprotecting a compound of Formula IV, wherein $R_1$ and $R_2$ are independently represents J or $C_{1-4}$ alkyl group, with an aluminum salt-amine complex in an organic solvent

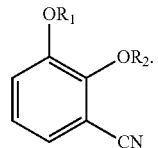

Formula IV

16. The process of claim 15, Wherein the $C_{1-4}$ alkyl is selected from the group consisting of methyl, ethyl, propyl, isopropyl, and ter-butyl.

17. The process of claim 15, wherein the aluminium salt is selected from the group consisting of aluminium chloride, aluminium bromide and aluminium iodide.

18. The process of claim 15, wherein the amine is selected from a compound of formula NRaRbRc;
wherein Ra, Rb and Rc independently represents a hydrogen, a linear or branched alkyl group, a linear or branched $C_2$-$C_6$ alkenyl group, a $C_1$-$C_6$ alkanol, a $C_3$-$C_{10}$ cycloalkyl group, a cycloalkylalkyl group, an aryl group, or an aralkyl group.

19. The process of claim 15, wherein the aluminium salt-amine complex is aluminium chloride-N,N-dimethylaniline complex or aluminium chloride-triethylamine complex.

20. The process of claim 15, wherein the organic solvent is selected from the group consisting of esters, ketones, amides, nitriles, ethers, halogenated hydrocarbons, aromatic hydrocarbons and mixtures thereof.

* * * * *